(12) United States Patent
Baumann et al.

(10) Patent No.: US 12,181,655 B2
(45) Date of Patent: Dec. 31, 2024

(54) OPTICAL SYSTEM FOR A VIDEO ENDOSCOPE AND VIDEO ENDOSCOPE

(71) Applicant: KARL STORZ SE & Co KG, Tuttlingen (DE)

(72) Inventors: Harald Baumann, Tuttlingen (DE); Benjamin Häsler, Tuttlingen (DE); Marcel Hofstetter, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 515 days.

(21) Appl. No.: 17/492,535

(22) Filed: Oct. 1, 2021

(65) Prior Publication Data
US 2022/0107492 A1    Apr. 7, 2022

(30) Foreign Application Priority Data
Oct. 2, 2020   (DE) .......................... 102020125854.2

(51) Int. Cl.
*G02B 23/24* (2006.01)
*G02B 1/12* (2006.01)
(Continued)

(52) U.S. Cl.
CPC ............. *G02B 23/243* (2013.01); *G02B 1/12* (2013.01); *G02B 3/0043* (2013.01); *G02B 5/28* (2013.01);
(Continued)

(58) Field of Classification Search
CPC ...... G02B 23/243; G02B 1/12; G02B 3/0043; G02B 5/28; G02B 13/0035;
(Continued)

(56) References Cited

U.S. PATENT DOCUMENTS 7,280,283 B1 * 10/2007 Kasai .................. G02B 9/60
                                                        359/656
8,432,611 B1    4/2013 Wach
(Continued)

FOREIGN PATENT DOCUMENTS

| EP | 1759628 A1 | 3/2007 | |
| EP | 2078976 A1 * | 7/2009 | ......... A61B 1/00096 |
| WO | 20190191497 A1 | 10/2019 | |

OTHER PUBLICATIONS

Sony, "Diagonal 4.60mm (Type 1/4.0) 8 Mega-Pixel CMOS Image Sensor with Square Pixel for Color Cameras IMX219PQH5-C," Instructional Literature, pp. 1-96, unknown date.
(Continued)

*Primary Examiner* — Michael Lee
(74) *Attorney, Agent, or Firm* — David N. Villalpando; Jacqueline Cohen (57) ABSTRACT

The invention concerns an optical system, and a video endoscope therefor, with at least one electronic active pixel image sensor with a progressive offset micro-lens array, and a lens system with a plurality of lenses in order to receive image light from an object field and direct it to the image sensor. The optical system has at least one interference filter coating located within the optical system, such that the angle of incidence of the image light on the filter coating is minimized, minimizing thereby the filtration characteristics of the coating that are angularly dependent. This minimization improves the reliability of fluorescence imaging with short optical systems. The location for the filter coating may be on a curved surface, such as a lens, or on a properly positioned flat element within the optical system.

20 Claims, 3 Drawing Sheets

(51) Int. Cl.
  *G02B 3/00* (2006.01)
  *G02B 5/28* (2006.01)
  *G02B 13/00* (2006.01)
(52) U.S. Cl.
  CPC ..... *G02B 13/0035* (2013.01); *G02B 23/2484* (2013.01)
(58) Field of Classification Search
  CPC ................ G02B 23/2484; G02B 5/283; G02B 2207/113; G02B 23/2423; G02B 23/2446; A61B 1/00096; A61B 1/00186; A61B 1/043; A61B 1/05
  See application file for complete search history.

(56) References Cited

U.S. PATENT DOCUMENTS

| | | | |
|---|---|---|---|
| 9,939,627 B2 | 4/2018 | Eguchi | |
| 2009/0290236 A1 | 11/2009 | Wang | |
| 2013/0155212 A1* | 6/2013 | Kamo | G02B 23/243 348/311 |
| 2014/0211073 A1 | 7/2014 | Shpunt et al. | |
| 2017/0235123 A1* | 8/2017 | Kamo | G02B 23/243 359/738 |
| 2017/0242237 A1* | 8/2017 | Eguchi | G02B 23/243 |
| 2019/0086647 A1* | 3/2019 | Kamo | A61B 1/0011 |
| 2019/0110686 A1 | 4/2019 | Kato | |
| 2019/0142249 A1 | 5/2019 | Koyama | |
| 2019/0187454 A1 | 6/2019 | Baba | |
| 2020/0064600 A1 | 2/2020 | Igarashi | |
| 2022/0104693 A1* | 4/2022 | Baumann | A61B 1/05 |

OTHER PUBLICATIONS

Obermeier, "Recherchebericht" (German Patent Office Search Report), Sep. 9, 2021, pp. 1-6, Deutches Patent- und Markenamt, Munich.
Artikis, T., "Communication" (Extended European Search Report), Feb. 23, 2022, pp. 1-6, European Patent Office, Munich.

* cited by examiner

OPTICAL SYSTEM FOR A VIDEO ENDOSCOPE AND VIDEO ENDOSCOPE

CROSS REFERENCE TO RELATED APPLICATIONS

This application claims priority to German Patent Application No. 102021106839.8, filed Mar. 19, 2021, and German Patent Application No. 102020125854.2, filed Oct. 2, 2020, both of which are incorporated by reference.

FIELD OF THE INVENTION

The invention concerns video endoscopes and optical systems therefor, and more particularly to video endoscopes used for visible and fluorescent imaging (FI). This invention is particularly relevant to distal tip video endoscopes with short optical systems and those wherein the image sensor is an active pixel sensor with a progressive offset of a micro-lens array.

BACKGROUND OF THE INVENTION

For medical or non-medical applications, endoscopes comprise an elongate shaft configured to be introduced into an internal cavity of a human or animal body or another object for examination, such as a piping. Non-medical endoscopes are often referred to as borescopes. For generating an image of an object field, an imaging optic is located in a distal (meaning distant from a user) end section of the shaft. Instead of traditionally used CCD (charge coupled device) sensors, It has become more common to use higher resolution electronic image sensors, such as CMOS (complementary metal-oxide-semiconductor) image sensors directly in the distal end section of the shaft. Besides the superior quality of the generated image by the highly resolving CMOS-sensor, this kind of sensor better meets the limited space available for the optical system within the distal end section, which commonly encourages the use of a single chip as image sensor, also placed within the distal end section. This type of video endoscope is sometimes referred to as a "chip on the tip," or COTT endoscope. Furthermore, in the modern electronics economy CMOS-sensors are frequently mass produced for ubiquitous applications such as smartphones and digital cameras, and therefore have become more available and less expensive. However, the micro-lens arrays prefabricated with the mass-produced CMOS sensors, for presumed use in cell phone and digital camera applications, have a steep chief ray angle (CRA) function. Therefore, the use of these prefabricated sensors, when attempts are made to use them in endoscopes, requires the optical system to spread the rays of the receive image light from the object field on the sensor plane of the image sensor to meet its steep chief ray angle. However, the combination of a short optical system and a commonly mass-produced CMOS-sensor in endoscopes causes specific problems concerning the progression of rays within the optical system that is particularly troubling to reliable fluorescence imaging.

In fluorescence imaging, it is necessary to filter out excitation radiation such that only the radiation emitted by the excited fluorophore is collected by the image sensor. This is especially important as the intensity of excitation light is usually higher than the emission light and therefore the fluorescence signal. In order to filter out the excitation radiation, it is possible to place an interference filter in a long and preferably telecentric optical system in a position where all main rays are incident on the interference filter near the same angle, so that a flexible positioning within the optical system of the interference filter is possible. Commonly, in long and telecentric or nearly telecentric optical systems, for example those including a CCD-sensor, an interference filter for enabling fluorescence imaging is placed between the optical objective system and the CCD-sensor near the cover glass of the sensor or near the most distal lens of the optical objective system, where all main rays have a low angle of incidence (AOI) and almost the same angle over the entire filter surface.

However, in endoscopes with a short optical system that meets the steep chief ray angle requirement of a CMOS sensor's micro lens array, such positioning of an interference filter is not possible. This creates a problem, as interference filters generally change their band of transmission as the angle of incidence diverges from a perpendicular to the surface of the interference filter. This affects the wavelength of peak transmittance, and therefore the filter edge is shifted towards shorter wavelengths, especially in the peripheral region of the image. Due to this shift towards shorter wavelengths, the commonly shorter excitation wavelength in fluorescence imaging can pass the interference filter and thus overlays and interferes with the emission wavelength from the fluorophore, resulting in unreliable fluorescence observation and imaging as well as false interpretation of the fluorescence signal. This can have major consequences, such as the inability to reliably recognize the boundaries of a tumor in a medical application or the proper detection of bacteria, for example, in industrial applications.

In short optical systems, due to the adaption of the objective to the high chief ray angle progression of the electronic image sensor and therefore the high angle of incidence within the optical system for a major part of the field of view, commonly known interference filters cannot be used, at least as conventionally positioned.

In general, commonly known interference filters can only be optimized for a specific angle of incidence and a specific wavelength.

Overcoming the wavelength transmission dependency of an interference filter is addressed in US 2014/0211073 A1 where an optical apparatus with an image sensor and an optical assembly for focusing optical radiation via an aperture stop onto the image sensor is suggested, in which the optical assembly comprises a plurality of optical surfaces, including a curved surface having a center of curvature in a vicinity of the aperture stop, and an interference filter comprising a coating is formed on this curved surface, the center of curvature of which is in the vicinity of the aperture stop. However, in this optical apparatus, lenses with high numerical aperture and therefore small F-numbers are used, such as 2, and wherein the angular spread of the rays increases with numerical aperture. However, the optical apparatus of US 2014/0211073 A1 considers electronic imaging systems in general and is not describing or focusing on endoscopes. Accordingly, this optical apparatus is concerned with the large AOI on the filter surface as a result of the small F number and hereby assume a CRA of zero.

By contrast, most endoscopes preferably have a larger F-number and therefore a higher ratio of the system's focal length to the diameter of the entrance pupil, in order to provide a more advantageous depth-of-field. Lower F-numbers are only used when depth-of-field is less important and instead bright image and high resolution is required in endoscopes. Consequently, endoscopes using standard CMOS-sensors containing micro-lens arrays must consider, not only, the angular spreading of the rays, but also the high chief ray angles required by the micro-lens array of the CMOS-sensor. This CRA requirement can be interpreted as a "field-dependent offset" of the AOI, making the problems associated with a large AOI much more challenging. As the optical apparatus of US 2014/0211073 A1 uses lenses in a telecentric configuration, an adaptation of the ray progression within the optical assembly to steep chief ray angles of a CMOS-sensor is not possible.

In US 2019/0187454 A1, an objective optical system for an endoscope is described which comprises a front group having a negative focal power and including only three lenses, an aperture stop and a rear group having positive focal power, likewise including only three lenses. In the front group, an optical member with a filter function can be disposed between the first lens and the second lens, wherein the optical member has parallel incident and emitting surfaces. This objective optical system serves to correct chromatic aberrations in a wide-angle lens system capable of observing a wider range and allowing an observation with a laser light source of 400 nm wavelength in addition to a white light source.

Likewise, in US 2019/0142249 A1, a special endoscope objective optical system including, in order from an object side, a front group having a negative refractive power, an aperture stop and a rear group having positive refractive power, wherein a multilayer optical interference film is integrated to almost 100% reflect a wave light of a neodymium yttrium aluminum garnet laser used for treatment of a tumor during endoscopic use. Due to the dependency of this multilayer optical interference film on the angle of incidence, it is necessary to locate this film at a location where an angle of incidence of a principal light ray does not become excessively large and therefore the film is disposed on the image side of the third lens having positive refractive power of the rear group.

What is therefore needed is an optical system for a video endoscope that is compatible with conventional CMOS sensor systems containing microlens arrays, and, in particular, one that is adapted to permit the reliable collection of both visible light images and FI images.

BRIEF DESCRIPTION OF THE INVENTION

The shortcomings of the prior art are solved by the presented, inventive optical system for a video endoscope that comprises at least one electronic image sensor, wherein the image sensor is an active pixel sensor with a progressive offset of a micro-lens array, and a lens system with at least one lens, a second lens, a third lens and/or further lenses in order from an object side to receive an image light from an object field and to direct the image light to the at least one image sensor arranged in an image plane of the optical system, where at least one filter coating is located at and/or on a support element for forming an interference filter at a position in the optical system, such that the angle of incidence of the image light on the filter coating is minimized and fluorescence imaging is thereby possible.

By positioning the filter coating within the optical system such that the angles of incidence of the image light on the surface of the filter coating are minimized, in a distal tip end endoscope with a short optical system where, in principle, the principal rays not perpendicularly incident on the surface of a component of the optical system nevertheless result in a distinct observation and display of the detected light by an electronic image sensor and also fluorescence imaging is enabled.

Therefore, fluorescence imaging, wherein no contamination by the excitation wavelength occurs on the detected fluorescence emission wavelengths due to the efficient absorption and/or blocking by the filter coating, is realized also in endoscopes with a short optical system using a electronic image sensor, such as a CMOS-sensor with a micro-lens offset array, and therefore a high chief ray angle, especially at the peripheral edges of the image sensor plane. Consequently, the optical system is useable, for example, in a colonoscope meeting the requirements of a high chief ray angle of a CMOS-sensor and simultaneously providing the performance of fluorescence imaging.

Therewith, a new camera system for an endoscope is provided in which largely obsolete CCD-sensors are replaced by high resolution CMOS-sensors. This is especially important, because the mass-produced CMOS-sensors are more cost efficient and easily available on the market, and also, in general, have a higher resolution and therefore enable higher quality imaging.

Due to the optimal position of the filter coating within the optical system with a minimization of the angle of incidence of the image light on the filter coating, a shift of the respective peak transmission and therefore the shift of the filter edge towards a shorter wavelength is diminished, and consequently an emission radiation of a fluorophore as collected by a larger area of the image sensor than heretofore possible is free of a contamination by the excitation radiation. In ideal implementations of the present invention, the entire image would be free of this contamination, however in other implementations some regions of the image may be contaminated, and these regions can be indicated as unreliable to the user.

Consequently, in a 2D video endoscope with a fluorescence optic, 2D white light imaging and 2D fluorescence imaging, 2D overlay display of fluorescence and visible light (white light) as well as 2D imaging of alternative fluorophores in overlay modes or pure fluorescence modes are possible. Likewise, for a 3D video endoscope with two separated fluorescence optics, 3D imaging of visible light, 3D imaging of alternative fluorophores and 3D overlay of fluorescence and visible light are realized.

Therewith, the fluorescence functionality of an endoscope is enhanced and optimized by the filter coating located within the optical system. Hereby, it is especially advantageous that only one electronic image sensor for the visible light and the fluorescence imaging is necessary, or two image sensors in case of 3D imaging.

Furthermore, an endoscope with a short optical system in its distal end tip is provided that is useable without any additional sensors or the changing of filters for visible light and fluorescence imaging.

By positioning the filter coating within the optical system at a position where the angles of incidence of the image light on the filter coating are minimized, the dependency on the angle of incidence of the interference filter, and corresponding filter edge shift to shorter wavelengths, is diminished, permitting, thereby, improved reliability in fluorescence imaging.

Furthermore, regardless of the interference filter within the optical system, the progression of the chief ray angles of the optical system are adapted to the chief ray angle progression of the electronic image sensor. This is especially important as this active pixel sensor with a progressive offset of the micro-lens array allows smaller pixels to which the light can be focused by means of the micro-lenses and therewith the light sensitive area and the sensitivity of the image sensor can be significantly increased.

One of the primary ideas of the invention is the special arrangement of a filter coating within an optical system, wherein the angles of incidence to the filter coating at and/or on a support element for forming an interference filter allowing fluorescence imaging is significantly lower than the respective high chief ray angle progression of the electronic image sensor with progressive offset of a micro-lens array. By the specific arrangement of this optical system, simultaneous fluorescence imaging and highly resolving CMOS-sensor technology may be achieved together. Furthermore, due to the design of the interference filter as a coating film, its integration within the short optical system of the endoscope saves valuable space.

As utilized in accordance with the present disclosure, the following terms, unless otherwise indicated, shall be understood to have the following meanings.

An "optical system" is in particular a system which includes one filter coating and an objective lens system to receive, pass forward and modify the image light from an object field to an image sensor. The optical system is in particular configured to be arranged at a short length in a distal end section of a shaft of the video endoscope. The optical system is, in particular, also a camera objective.

The "lens system" comprises in an order from an object side a cover glass and/or a first lens, a second lens and/or further lenses, which are arranged along an optical axis of the lens system. For example, in between the first and the second lens of the objective lens system, the filter coating can be located. A "lens" in particular is a transmissive optical body that focusses or disperses a light beam (light rays) by means of refraction. The first lens, the second lens, the third and further lenses can be single lenses, which are separated by an air gap or are in contact to adjacent lenses at most pointwise. Also, one lens can be a combined lens, a rod lens or a compound lens. For example, a compound lens has single optical elements, which are cemented to each other. Different compound lenses are in particular separated by air gaps and/or are in contact at their vertexes. In a design of single lenses, these single lenses can be mounted by a functional rim around the respective lenses together. At least one lens of the lens system has a positive refractive power, preferably the lens system comprises at most three lenses. For many endoscopic applications, F-numbers between 2 and 14 are preferable, which in general depends on the requirements on brightness of the image, the required resolution and depth of field. Preferably, the lenses are made of glass and/or a crystalline material. Also, one lens or more lenses can be made from optical ceramics. At least one lens has preferably a refractive index n approximately equal to or exceeding 1.6, preferably exceeding 1.7 or even 1.8. At least one lens has preferably an Abbe number v exceeding 70, preferably exceeding 80. In some embodiments one or all lenses of the objective lens system may be aspherical and/or some or all optical surfaces of the lenses may be aspherical. The aspherical surface maybe convex, concave, and/or may comprise convex, concave and/or plane portion, the aspherical surfaces offering advantages in controlling the sensor CRA and filter AOI. Preferably, the aspherical surfaces are rotationally symmetric and the axis of symmetry of the lenses are aligned with each other and/or with the optical axis of the objective lens system. In other embodiments, all surfaces are spherical, simplifying the manufacturing and expense of the optical system. Preferably the lens system comprises an aperture stop. The aperture stop can be formed by a black coating, which is positioned on a surface of a plan parallel glass plate. Therein, the black coating forming the aperture stop is able to suppress white light, the excitation source and/or the fluorescence signal. As an alternative, the aperture stop can also be realized by a mechanical structure.

The first lens is preferably a front lens with a high refraction of the steep rays coming from the object field. By this refraction, the front lens preferably decreases the angle of incidence on the subsequent optical elements. The first lens of the optical system can be for example a plano-concave lens or a cover glass with a concave depression facing with a concave side towards the image sensor.

A "video endoscope" (also denominated simply as "endoscope") is an endoscope with a digital image acquisition and transmission into the proximal end of the video endoscope. The video endoscope comprises an elongate shaft and a handle which are connectable to each other. At least one digital image sensor is located at the distal end (and therewith the side in a distance from the user of the video endoscope) of the elongate shaft for image acquisition. In particular, the video endoscope is any kind of digital endoscope, for example a 2D colonoscope or gastroenteroscope or a 3D video endoscope with, for example, two separated fluorescence objectives. The video endoscope is in particular a chip-on-the-tip (COTT) endoscope, wherein the image sensor as one chip is arranged in the distal end section of the shaft of the video endoscope and the image data collected by the image sensor are transmitted electronically through the shaft towards the proximal side and further to a display system and/or an image processing unit to display the endoscopic image for the user. In particular, in such COTT endoscopes, the objective lens system is employed having a long extension in an axial direction to achieve a near telecentric path. However, the available space in the distal end section of the shaft is limited and therefore a short optical system and/or a short objective lens system is preferable to a conventional system with a long extension and is positioned in front of the image sensor. The video endoscope can be reusable and autoclavable, especially as a medical video endoscope.

The "elongate shaft" is in particular a rigid, semi-flexible or flexible tube. In particular, the shaft is configured for being inserted into a cavity to be viewed endoscopically, for example a body cavity of a human or animal body or another opening in industrial applications, for example a pipe. Generally, the shaft may have an outer diameter in the range of 4 mm to 10 mm. Besides the optical system and one or two image sensors, the shaft may comprise one or more channels for irrigation or passing through working instruments (generally referred to as "working channels") in order to achieve the desired effect in the cavity or opening. Therefore, space requirements in the distal end section of the shaft are further limited by further components, such as illumination light guides, optics, and instrument channels in addition to the optical system. The shaft can be connected at its proximal end to a handle of a video endoscope or be permanently connected to a handle. Therefore, the shaft may be separately disposable including the optical system, the objective lens system and/or the image sensor.

A "electronic image sensor" has, in particular, its sensor plane in an image plane of the optical system and/or the lens system. The electronic image sensor is in particular a complementary metal-oxide-semiconductor (CMOS). Preferably, the electronic image sensor is a high-definition (HD) image sensor having, for example, full HD resolution. More preferably the electronic image sensor may be of higher resolution than full HD, for example a resolution of 5 mega-pixel (5MP). Additionally, 4K resolution sensors, or higher, may also be enabled in some embodiments. In general, the electronic image sensor is configured to convert the captured image into a digital and therewith electronic image signal and therefore image data. In particular, the electronic image sensor is arranged preferably as a chip directly in the distal end section and/or the tip of the shaft of the video endoscope and transmits the digital image signals from the distal end of the shaft to its proximal end by electric transmission lines, such as wires, cables and/or a flexible printed circuit board. Preferably, from the shaft, the electric image signals generated by the electronic image sensor are transferred further to the handle of the video endoscope and/or a display system and/or a processing unit for displaying the captured images. The electronic image sensor can be a mass-produced highly resolving image sensor, for example as used in smartphones, which includes a micro-lens array with a relatively steep chief ray angle (CRA), wherein the chief ray angle is particularly varying with the increasing distance from an optical axis of the optical system and/or objective of the video endoscope. In particular, the micro-lens array arranged on a distal side of the electronic image sensor has a nonlinear CRA function and the optical system and/or the lens system is adapted to the respective CRA function of the electronic image sensor. Therefore, the diverging and spreading of the light rays within the optical system is required due to the steep chief ray area of the electronic image sensor, especially a CMOS-sensor.

A "progressive offset of a micro-lens array" means in particular that the micro-lenses are progressively offset, often non-linearly, towards an optical center point of a sensor array of active areas (pixels) as a distance from the respective active area to the optical center point increases, wherein in particular the progressive offset varies with the distance. Often the CRA functions of CMOS-sensors are nonlinear and are reaching a maximum value at a relatively large image height, wherein between the maximum value and the maximum image height (e.g. the image corner) the CRA function decreases slightly.

An "interference filter" is in particular a device which selects the incident radiation and/or rays based on specific criteria, such as the wavelength, the polarization state and/or the incident angle or direction. The interference filter is particularly used as an observation and/or detection filter within the optical system. The interference filter can be, for example, a gradient filter with a continuously or discontinuously changing filter effect over the filter surface from the center to the peripheral region or can be an edge filter with two or more spectral ranges distinctly sharply separated from each other in which the edge filter transmits (and therefore is transparent) or absorbs (and therefore is non-transparent). An edge filter is also a long pass filter (cut-off filter). The interference filter can also be an interference filter or dichroic filter, which is an interference filter that reflects one or more spectral beams or lines and transmits others while maintaining an almost zero coefficient of absorption for all wavelengths of interest. An interference filter comprises in particular a filter coating and/or multiple thin layers of dielectric material having different refractive indices. The interference filter is in particular wavelength-selective due to the interference effect that occurs between the incident and the reflected waves at the thin layer boundaries. The interference filter comprises in particular a coating which effects a blocking and/or transmission of the respective light. Preferably, the interference filter completely blocks the excitation light while it transmits the fluorescence emission light with preferably a longer wavelength. Commonly, the interference filter selects a narrow band of incidence angles and corresponding specific wavelength. Interference filters are usually optimized for a small range of AOIs, resulting in changes to the filter spectrum with larger AOI deviations. The interference filter comprises glass and/or a crystalline material.

A "filter coating" is in particular an interference filter coating. The filter coating can be a thin film located at and/or on a support element for forming the interference filter. In particular, the filter coating is a durable optical thin-filmed coating. For example, the filter can be located and/or mounted at and/or on the support element by a specialized coating process, such as a reactive sputtering process, a low-pressure chemical vapor deposition, evaporation, and other suitable processes. Furthermore, the filter coating can be produced as a thin film and located on or at the support element. The filter coating in particular consists of one thin layer or multiple thin layers having different refractive indices. In particular, the filter coating comprises a dielectric material, metals, metal oxides, nitrides, semiconductor material and/or other suitable materials.

As "support element" is especially an element inherent of the optical system, such as a lens or another optical component, or specifically inserted into the optical system for carrying the filter coating. Preferably, the filter coating is applied and located directly on the surface of a support element. Also, the filter coating does not have to cover completely the support element, for example, the filter coating can only touch a rim of a lens. Also, the support element can be a frame, in which the filter coating as a film is mounted. Preferably, the support element is an already necessary existing component of the optical system for obtaining a space-saving short optical system. Preferably the filter coating is placed on one surface of the support element, e.g. a glass plate, for blocking the excitation source and on the opposite surface an anti-reflection coating is placed.

The "angle of incidence" (AOI) is in particular the angle between a ray incident on a surface and the line perpendicular to the surface at the point of incidence, wherein the line is called the "normal". The angle of incidence is in particular the angle between a ray incident on the surface of the filter coating to the normal. This normal can also be the optical axis or be parallel to the optical axis.

The "optical axis" is in particular a line along which some degree of rotation symmetry exists in an optical system. The optical axis in particular is an imaginary line that defines the path along which light propagates through the optical system and the objective lens system towards the electronic image sensor. Preferably, the optical axis passes through the center of curvature of each lens, the filter coating and/or the successive lens. However, the optical axis can also be bent and/or directed by the lenses and/or the filter coating.

"Fluorescence" is in particular an emission of light by a substance (fluorophore) that has absorbed light or other electromagnetic radiation. In particular, the fluorophore is irradiated with a specific excitation wavelength or wavelength band to emit light with a specific emission wavelength or wavelength band. Normally, the emission wavelengths are longer than the excitation wavelengths. For excitation, for example, light in the UV region of spectrum is used, while the emission radiation is in the longer wavelength band and therefore in the visible region having lower energy. Depending on the fluorophore, the emission radiation can be seen as a distinctive color. For fluorescence imaging, biological material, such as a tissue for finding a tumor in a body cavity or a bacterium in the environment, is dyed with a fluorophore directly or by administered a substance which is converted into the fluorophore by the body or microorganism before using the video endoscope. By an illumination source and/or filter, an excitation wavelength range is irradiated, for example by an optical fiber, at the distal tip of the shaft on the fluorophore and the emission wavelength range of the fluorophore emitted by the tissue with the tumor is captured by the optical system including the objective lens system and the filter coating and transmitted to the image sensor. A "fluorophore" can, for example, be indocyanine green, which absorbs light as well as emits fluorescence in the near infrared range. The excitation wavelength range of indocyanine green is between 600 nm and 900 nm and the emission wavelength range between 750 nm and 950 nm. Other possible fluorophores include protoporphyrin IX (PPIX) with an excitation wavelength range around 405 nm and an emission wavelength range of around 620 nm to 700 nm or fluorescein with a maximum excitation wavelength of 488 nm and an emitted fluorescence in the green spectral range from 500 nm to 600 nm. Additionally, two fluorophores can be used together and therefore dual fluorescence imaging is possible. For this, a 3D video endoscope comprises two separate fluorescence objectives and therefore two optical systems as described above, allowing photodynamic diagnostics and imaging. In general, fluorophores can be used, and fluorescence imaging can be conducted, with a fluorescence emission preferably outside of the typical visible range of approximately 450 nm to 650 nm. Certainly, also auto fluorescence of a tissue or an environment can be measured without previous colorization by a fluorophore or dye.

In another embodiment of the invention, the optical system comprises a second filter coating, a third filter coating, a fourth filter coating and/or further filter coatings.

By this, a multilayer optical interference filter is formed as well as different transmission and blocking properties are realizable, for example, in fluorescence imaging using two or more different fluorophores and/or also detecting autofluorescence of the tissue or bacteria.

The second, third, fourth and/or further filter coatings corresponds in its function and embodiment to the above defined filter coating.

For locating the filter coating optimally in respect to the specific power of each lens or the lenses and to the angle of incidence, the filter coating or the filter coatings is or are each located adjacent to one lens and/or in between two lenses of the lens system.

In a further embodiment of the invention, the filter coating or the filter coatings is or are located on an optical surface as support element of the optical system.

By locating the filter coating directly on an optical surface of the optical system, a space saving interference filter can be accomplished allowing a short optical system. It is especially advantageous that no interference filter as a separate component has to be inserted into the optical system, which would extend the length of the optical system. As the filter coating is very thin, it has no special space requirement. For example, the thickness of the filter coating can be in a range of 0.05 µm to 50 µm.

Therefore, the filter coating or filter coatings can be deposited on an optical surface which is specifically selected such, that the angles of incidence on the filter coating or the filter coatings are minimized. Furthermore, due to the direct location of the filter coating or the filter coatings on the optical surface, also the respective angles of incidence are clearly defined.

An "optical surface" is in particular a surface within the optical system which transmits and/or reflects light. In particular, the optical surface is a planar, spherical, and/or aspherical optical surface. In case of combined lenses, compound lenses and/or rod lenses, the optical surface can also be the outer side of the combined lens, compound lens or rod lens directed towards the objective side or the side towards the image sensor.

Depending on the components and arrangement of the components within the optical system, the filter coating or the filter coatings is or are located on a planar, spherical, or aspherical optical surface.

Therefore, the angle of incidence to the filter coating or filter coatings can be kept as small as possible, preferably 0° or at least smaller than the CRA progression of the image sensor to avoid falsification of the transmission spectrum and to enable an efficient blocking of the excitation light in fluorescence imaging.

In certain preferred embodiments, the filter coating or filter coatings are located on a curved surface of the optical system, because, due to the curved surface, the normal to the surface varies and thus the angle of incidence of peripheral rays is much closer to 0 than on a flat surface. Consequently, the angle of incidence remains closer to perpendicular incidence with increasing field of view, preferably close to 0° over the entire field of view.

In another embodiment, the optical system can comprise an optical plate as a support element, wherein the filter coating is, or the filter coatings are, arranged at least on one side of the optical plate.

Therewith, a flat interference filter can be formed. As the front lens has normally a high refractive power converging the steep rays from the object field towards and along the optical axis, the optical plate as a support element can be arranged directly on the image side of the front lens as the first lens and/or between the first lens and the second lens of the optical system.

An "optical plate" is, in particular, a flat and/or even component, which comprises glass and/or crystalline material, or, additionally, optical ceramics may be used as the optical plate. In the direction along the optical axis, the optical plate has preferably a low dimension in order to keep the length of the optical system, and in particular a short optical system, to a minimum.

In order to minimize the influence of the diverging angle of incidence on the bandwidth of transmission by the interference filter, the angle of incidence of the image light on the filter coating or filter coatings is <30°, preferably <20°, most preferably <10° or 0°.

Therefore, a specific angle of incidence on the filter coating or filter coatings can be chosen depending on the possible position of the filter coating or the filter coatings within the optical system, on the required fluorescence wavelength properties and the adaption of the progression of the rays within the optical system in order to meet the requirements of the steep CRA function of the image sensor.

For example, in case of a planar surface as support element for the filter coating, an angle of incidence <5° can be realized. Certainly, the function of the interference filter formed by the filter coating and the support element can also be sufficient with an angle of incidence of 10° or 12.5° or even higher. The tolerable angular shift of the AOI depends strongly on the light source spectrum, the fluorophore used, and the particular filter characteristics. In certain embodiments for ICG imaging and particular light sources, AOIs at the filter surface of lower than 10° are preferred.

In a further embodiment of the optical system, the filter coating or the filter coatings is or are formed such, that in case of fluorescence imaging, an emission radiation is collectable by the image sensor free of an excitation radiation.

Therewith, the filter coating or the filter coatings are located at an optimal position and have adapted transmission properties and/or filter edges to select between excitation and emission wavelengths, so that a shift of the respective peak transmission and of a filter edge to a shorter wavelength is avoided. Consequently, an emission radiation of a fluorophore is collected by the image sensor free of an interference by the excitation radiation, whereby the latter is blocked by the filter coating. Therewith, fluorescence imaging with one fluorescence or more fluorescence markers, such as indocyanine green, is possible with a high resolution as well as the detection of autofluorescence of a tissue is enabled. Therefore, a tumor in a tissue can be detected by gastro- and colonoscopy with the video endoscopy.

For covering a radially and/or outwardly changing angle of incidence, the filter coating or the filter coatings is or are adapted to the angle of incidence of the image light to the filter coating or filter coatings, in particular to a change of the angle of incidence from a center to a peripheral region of each filter coating or filter coatings.

Therefore, even if the filter coating or the filter coatings on the support element cannot be located within the optical system at an optimized position, where the angle of incidences of all rays are equally narrow over the surface of the filter coating, by adapting the filter coating to the angle of incidences, likewise a reliable fluorescence imaging can be achieved.

In a further embodiment, the micro-lens array has a high chief ray angle function with a high maximum angle of incidence of >10°, preferably >20°, more preferably >30°.

By this, reliable fluorescence imaging is also enabled by a commonly available standard CMOS-sensor with an integrated offset micro-lens array and a steep CRA.

The "chief ray angle (CRA)" of the micro-lens array and therewith the image sensor is in particular the angle between the chief ray of a given object field and the optical axis in the image space. The CRA progression gives in particular the dependency of the chief ray angle on the image height at the sensor array. The CRA progression of mass-produced CMOS-sensors, for example a smartphone objective, is normally not linear and increases to high values at the image border. In particular, the optical system is designed to be adapted to the steep CRA and to the increasing CRA from the middle of the sensor area towards the outer image border.

For meeting the requirements by a steep CRA of the image sensor, the filter coating, the filter coatings, the lenses and/or the support element are arranged such, that a path of rays of the optical system is adapted to the chief ray angle of the micro-lens array of the image sensor.

In a further embodiment of the optical system, the filter coating or the filter coatings comprises or comprise a varying transmission characteristic from a center to a peripheral region of each filter coating or the filter coatings.

Additionally, the filter coating can comprise different successive region from the center to its peripheral border which are each adapted to specific angles of incidence. For example, three distinct zones can be arranged from the center to the peripheral region of the filter coating which are each adapted to increasing angles of incidence.

In another aspect of the invention, the problem is solved by a video endoscope, in particular medical or industrial video endoscope, with a handle, an elongate shaft, a light source, an electronic image sensor and/or a display system, wherein the video endoscope comprises an optical system as described above in a distal end section of its elongate shaft.

Consequently, a video endoscope is provided, such as a colonoscope or a gastroscope, with a reliable fluorescence imaging and simultaneously a high image resolution due to the use of an electronic image sensor as an active pixel sensor with a progressive offset of its micro-lens array. Therewith, a photodynamic diagnostic is enabled in medical applications of the video endoscope as well as the detection, for example of different bacteria, in industrial applications of the video endoscope.

The invention is further explained by the following exemplary description of particular embodiments and the figures.

DETAILED DESCRIPTION OF THE INVENTION

Figure 1:
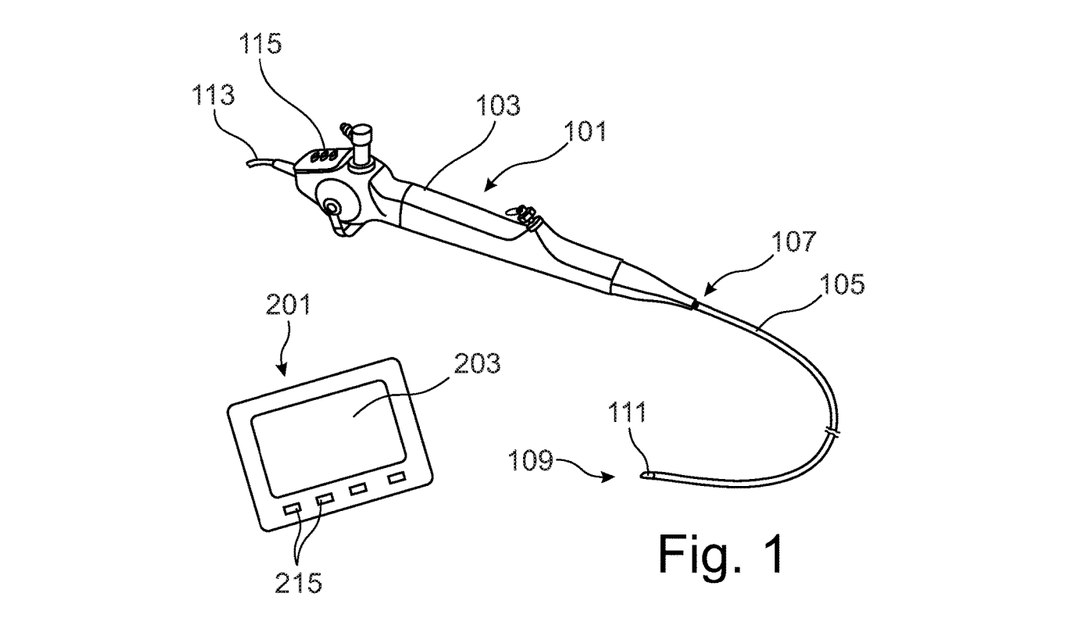
FIG. 1 is a schematic partial three-dimensional view of an endoscope and a display system.

A video endoscope 101 shown in FIG. 1 comprises a handle 103 and an elongate shaft 105 connectable to each other at a proximal end 107 of the shaft 105. The handle 103 comprises operator controls 115 and is connected via a cable 113 at its proximal end to an external, non-shown control and processing unit and to a display system 201 shown in FIG. 1. The display system 201 includes a monitor 203 for displaying endoscopic images and operator controls 215.

The video endoscope 101 is designed to provide video and image data from an object field within a cavity of a non-shown body. For this, the elongate shaft 105 comprises, at its distal end 109, a distal end section 111.

The distal end section 111 of the elongate shaft 105 comprises an optical system 301, as shown in FIGS. 2-5, and an image sensor 353 with a glass plate 351. The optical system 301 comprises an objective lens system 303 with a first lens 305, second combined lenses 311 and third combined lenses 323 in direction from an objective side 355 to the image sensor 353. The first lens 305 is designed as a front lens with a planar side 307 directed to the objective side 355. On the opposite side of the front lens 305, a concave side 309 is arranged. On a rim surrounding this concave side 309, an interference filter 331 is mounted, which is formed by a coating 345 arranged on the first planar side 335 of a glass plate 333. The glass plate 333 is arranged with its second planar side 337 in a distance to a convex side 313 of the second combined lenses 311. The second combined lenses 311 include four lenses cemented to each other with a convex surface 315 of its first lens cemented to a corresponding concave surface of its second lens, a planar surface 317, another planar surface 319 and a convex side 321 direct towards the image sensor 353. On the planar surface 317 a black coating 343 forming an aperture stop is positioned and providing an aperture 341 in its center. The convex side 321 of the second combined lenses 311 are adjacent directly to an opposite oriented convex side 325 of the third combined lenses 323. The third combined lenses 323 comprise two lenses cemented to each other, wherein a convex surface 327 of its first lens is cemented to the concave surface of its second lens. A concave side 329 of the third combined lenses 323 is directed to the image sensor 353. On the concave side 329, the third combined lens 323 is spaced by an air gap to the glass plate 351 of the image sensor 353.

The optical system 301 with the lens system 303, the interference filter 331 and the image sensor 353 are designed as a short optical system for the video endoscope 101. The image sensor 353 is a CMOS-sensor with a steep chief ray angle.

By a non-shown light source and a non-shown fiber optical cable of the video endoscope 101, illumination light and excitation light are radiated on an object field within the body cavity. A tissue in the body cavity has previously been colored by indocyanine green (ICG) and consequently a maximum peak of 795 nm is used for excitation. The indocyanine green emits fluorescence light with a maximum peak at 810 nm, so that the maximum excitation wavelength 795 nm and the emission wavelength 820 nm are very close together.

Figure 2:
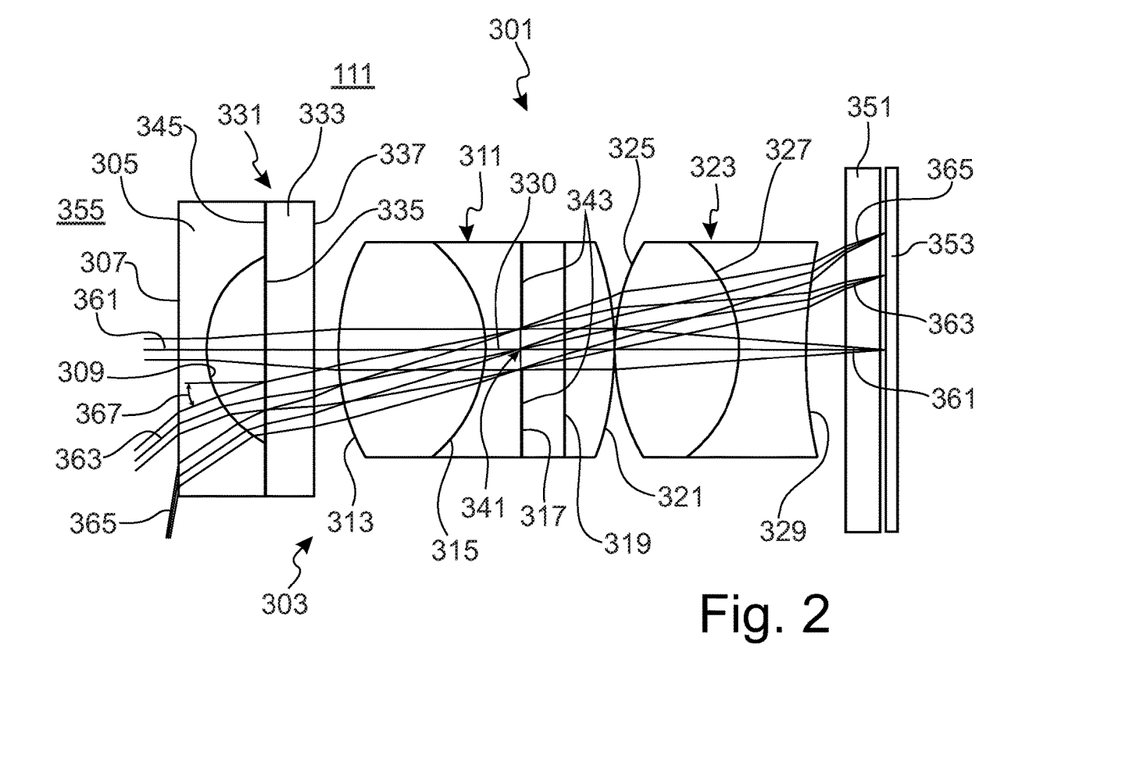
FIG. 2 is a schematic section view of an optical system with a coating on a glass plate forming an interference filter.

Due to the positive refractive power of the first front lens 305, the steeper light rays 363 and 365 coming from an object field associated with a ray bundle are converged by the concave side 309 of the first front lens 305 and incident on the coating 345 on the first planar side 335 of the interference filter 331, whereby the maximum angle of incidence 367 of the light rays with a high AOI 365 shown in FIG. 2 is approximately 22° on the surface of the filter coating 345 (corresponding to the angle measured in air between the concave side 309 of the front lens 305 and the filter coating 345). Therefore, light rays with a low angle of incidence (AOI) 361, light rays with a medium angle of incidence 363 and light rays with a high AOI 365 incident overall with a rather low angle of incidence on the coating 345 on the first planar side 335 of the interference filter 331. Afterwards, due to the refraction by the convex side 313 and the convex surface 315, the light rays 361, 363 and 365 come closer to and along the optical axis 330 at the planar surface 317 of the second combined lenses 311. The black coating 343 forming the aperture stop suppresses white light, the excitation source as well as the fluorescence signal, while the light rays 361, 363 and 365 passes through the aperture 341. Subsequently, by means of the convex side 321 of the second combined lenses 311 and the convex side 325, the convex surface 327 and the concave side 329 of the third combined lenses 323, the light rays 361, 363 and 365 are diverged towards the glass plate 351 in order to meet the requirements of the steep chief ray angle (CRA) of the non-shown micro-lenses of the CMOS image sensor 353 with a resolution similar to that of standard HD resolution or better, for example 2592×1944 pixels, although in certain embodiments, the resolution could be still greater (see FIG. 2).

Due to the interference filter 331 formed by the glass plate 333 with the coating 345 on the first planar side 335, the excitation light is blocked by the interference filter 331 and only the emission light by the fluorophore (for example, ICG with an emission wavelength of 820 nm) in addition to white light, when the image scene is appropriately illuminated in white light mode, is transmitted by the lens system 303 to the CMOS image sensor 353. Consequently, a reliable fluorescence imaging is carried out with the optical system 301 in the distal end section 111 of the video endoscope 101.

Figure 3:
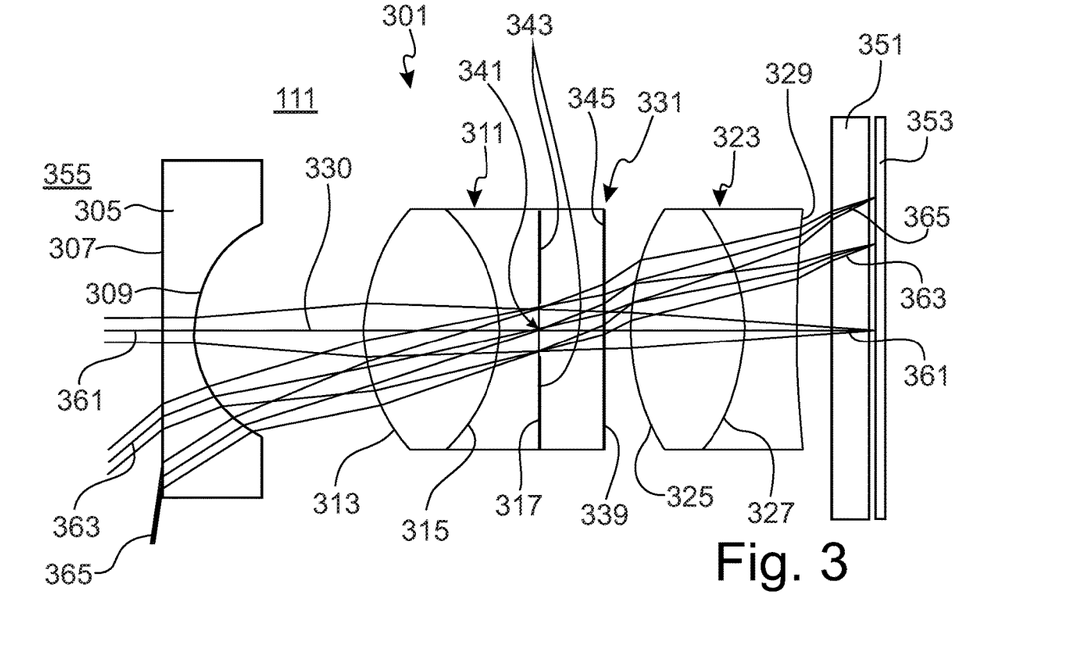
FIG. 3 is a schematic section view of an alternative of an optical system with a coating of a planar side of a combined lens forming an interference filter.
Figure 4:
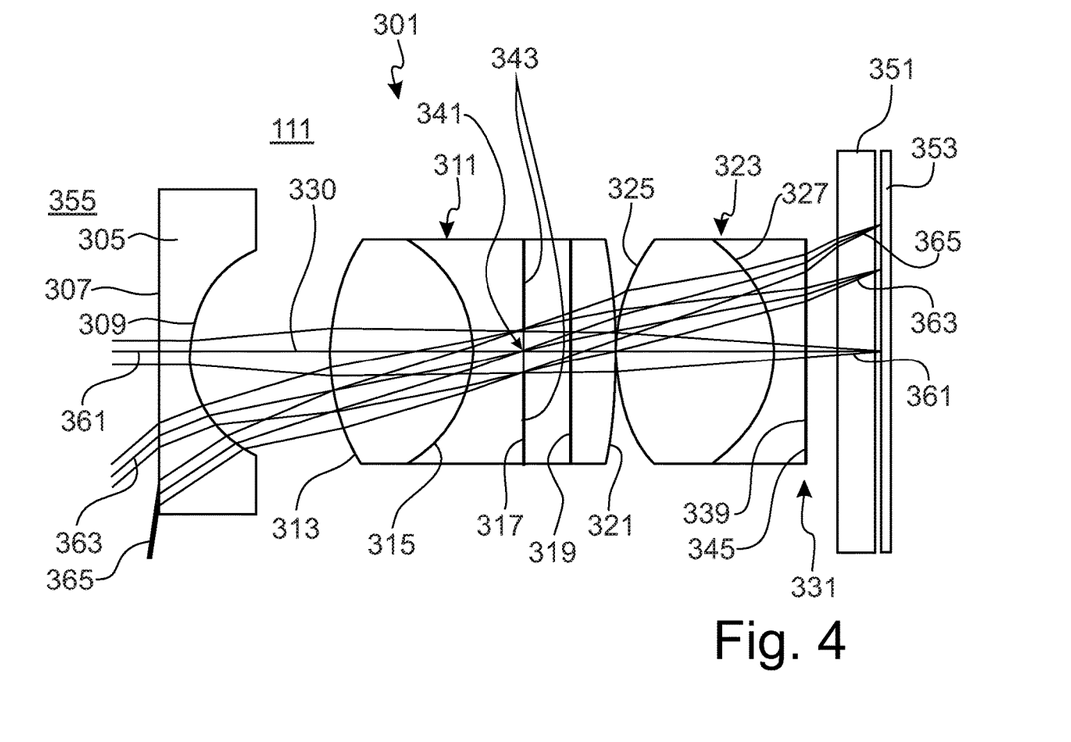
FIG. 4 is a schematic section view of a further alternative of an optical system with a coating on a planar side of a combined lens directed towards an image sensor.
Figure 5:
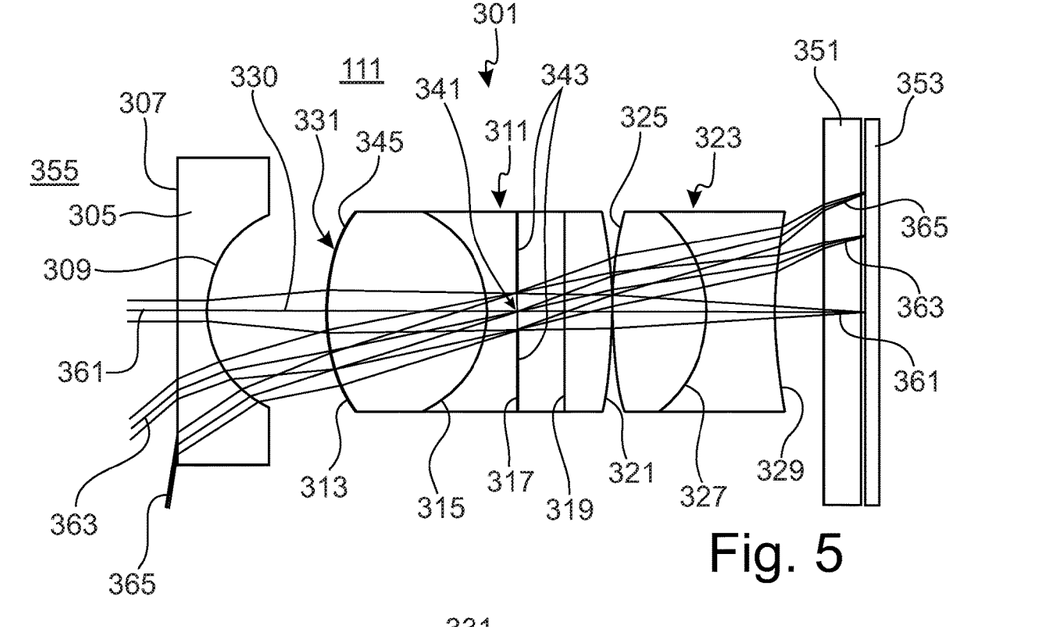
FIG. 5 is a schematic section view of a further alternative of an optical system with a coating on a convex side of a combined lens directed to an object side.

In an alternative embodiments, an optical system 301 comprises a first front lens 305 with a planar side 307 directed to the objective side 355 and a concave side 309 directed towards the image sensor 353 (see FIG. 3). In this case, the front lens 305 is set in a distance with an air gap in between to the second combined lenses 311, which comprises a convex side 313 directed towards the objective side 355, a convex surface 315, a planar surface 317 with a black coating 343 and an aperture 341 and a planar side 339. The planar side 339 is directed along the optical axis towards the second combined lenses 323. On the outside of this planar side 339, a coating 345 has been deposited giving an alternative interference filter 331. The second combined lenses 323 are designed as described above for FIG. 2, with the exception that a length of the second combined lens 323 along the optical axis 330 is shorter and a curvature of the convex surface 327 is smaller than shown in FIG. 2. Likewise, the CMOS image sensor 353 is formed and functions as described above.

In a further alternative of the optical system 301 (see FIG. 4), a front lens 305 is designed as described for FIG. 3 and its concave side 309 directed towards the second combined lenses 311 is likewise spaced to the convex side 313 of the second combined lenses 311. Furthermore, the second combined lenses 311 comprise a convex surface 315, a planar surface 317 with an aperture 341 and a surrounding black coating 343, and a planar surface 319 and a convex side 321 directed towards the third combined lenses 323. Hereby, the convex side 321 of the second combined lenses 311 and the convex side 325 of the third combined lenses 323 are directly adjacent to each other. The third combined lens 323 comprises further a convex surface 327 and a planar side 339 directed towards the CMOS image sensor 353. On this planar side 339, a coating 345 is applied to form an interference filter 331. Nevertheless, that in this alternative embodiment, the interference filter 331 is located close to the CMOS image sensor 353 and despite that the light rays with different AOI 361, 363 and 365 are already diverged by the second combined lens 311 to meet the requirements of the high chief ray angle of the micro-lens array of the CMOS image sensor 353, the light rays with a low AOI 361, the light rays with medium AOI 363 and the light rays with high AOI 365 are each close to each other, so that by this optical system 301, a reliable fluorescence imaging as well as a high resolution imaging by the CMOS image sensor 353 is realized in the image center. Despite this position of the interference filter 331 directly in front of the CMOS image sensor 353, the relevant angles for the filter performance correspond to the angles in air and therefore the surface angles of exitance of the light rays 361, 363 and 365 exiting from the coating 345 are converged and meeting the angles of incidence by the high CRA progression within the CMOS image sensor 353.

In another alternative of the optical system 301 shown in FIG. 5, again a first front lens 305 is distanced at its concave side 309 towards a convex side 313 of the second combined lenses 311. In this embodiment, the filter coating 345 is located directly on the convex side 313 of the second combined lens 311 forming an interference filter 331. The second combined lenses 311 and the third combined lenses 325 are designed as described above for FIG. 2. Due to converging the light rays with different AOI 361, 363 and 365 by the positive refracting power of the first front lens 305 towards the second combined lenses 311 and along the optical axis 330, the rays incident on the filter coating 345 at the convex side 313 of the second combined lenses 311 with a relatively small angle of incidence. Therefore, a colonoscope objective is provided by this optical system 301 with a field of view of 160° which allows fluorescence imaging and is simultaneously adapted for the high CRA progression of the CMOS image sensor 353.

Figure 6:
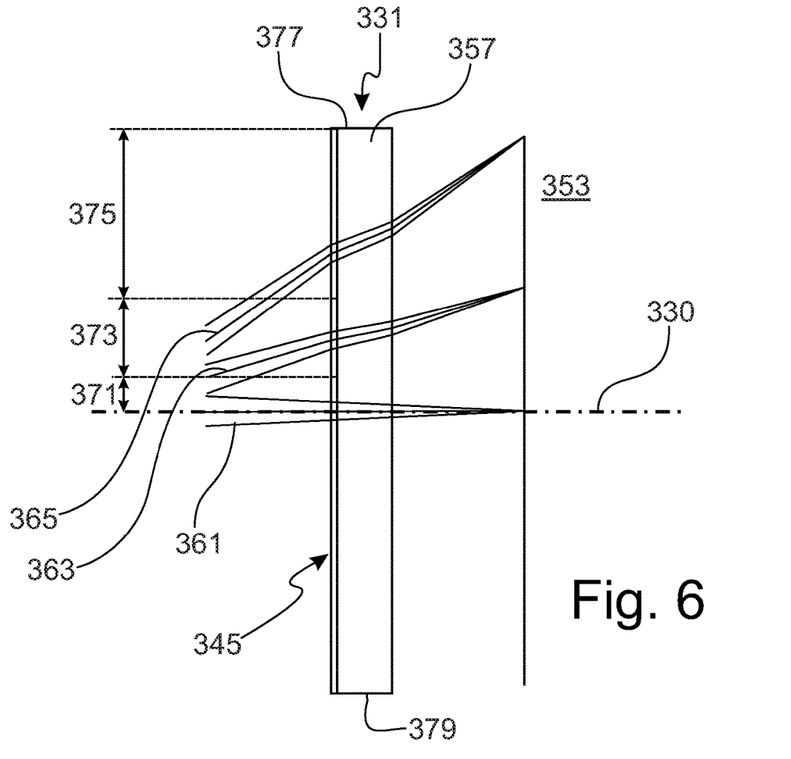
FIG. 6 is a schematic section view of an interference filter with different coating zones optimized for different angles of incidence.

In yet another inventive alternative of the interference filter 331 (see FIG. 6), the interference filter 331 comprises an optical flat substrate 357 and is placed in front of a CMOS image sensor 353 such, that the light rays with low AOI 361, the light rays with medium AOI 363 and the light rays with high AOI 365 have significantly different angles of incidence towards each other. In order to adapt the transmission properties of the interference filter 331 to these different angles of incidence of each light rays with different AOI 361, 363 and 365, the filter coating 345 applied on the side of the optical flat substrate 357 which is directed towards the objective side and therefore opposite to the CMOS image sensor 353 has, from the optical axis 330, first a coating zone optimized for low AOI 371 adapted to the light rays with low AOI 361, then followed by a coating zone optimized for medium AOI 373 adapted to light rays with medium AOI 363 and outwardly a coating zone optimized for high AOI 375 adapted to the light rays with high AOI 365 until a upper rim 377 of the interference filter 331. In FIG. 6, these three different zones 371, 373 and 375 are only shown for an upper part until the upper rim 377 of the interference filter 331 starting from the optical axis. The same order of zones is reversely arranged for a non-shown lower part below the optical axis 330 (shown in FIG. 6) with first the coating zone optimized for low AOI 371, the coating zone optimized for medium AOI 373 and the coating zone optimized for high AOI 375 ending at a lower rim 379. Therefore, by the interference filter 331 in this embodiment with a zoned coating 345, a multi-zone interference filter 331 is provided, which is adapted to light rays of different angles of incidence. Therewith, an adaptation of the transmission properties of the interference filter 331 to the angular, radially changing angle of incidence is achieved.

REFERENCE NUMERALS

101 video endoscope
103 handle
105 elongate shaft
107 proximal end of shaft
109 distal end of shaft
111 distal end section
113 cable
115 operator controls
201 display system
203 monitor
215 operators controls
301 optical system
303 lens system
305 front lens
307 planar side
309 concave side
311 combined lenses
313 convex side
315 convex surface cemented to concave surface)
317 planar surface
319 planar surface
321 convex side
323 combined lenses
325 convex side
327 convex surface (cemented to concave surface)
329 concave side
330 optical axis
331 interference filter
333 glass plate
335 first planar side
337 second planar side
339 planar side
341 aperture
343 black coating (aperture stop)
345 coating
351 glass plate
353 CMOS image sensor
355 objective side
357 optical flat substrate
361 light rays with low AOI
363 light rays with medium AOI
365 light rays with high AOI
367 angle of incidence (AOI)
371 coating zone optimized for low AOI
373 coating zone optimized for medium AOI
375 coating zone optimized for high AOI
377 upper rim
379 lower rim

The invention claimed is:

1. An optical system for a video endoscope comprising at least one electronic image sensor, wherein the image sensor is an active pixel sensor with a progressive offset of a micro-lens array and a chief ray angle function with a maximum angle of incidence of at least 20°, and a lens system with a first lens, a second lens, a third lens and/or further lenses in order from an object side to receive an image light from an object field and to direct the image light to the image sensor arranged in an image plane of the optical system, wherein at least one filter coating is located at and/or on a support element for forming an interference filter at a position in the optical system, such that an angle of incidence of the image light on the filter coating is minimized.

2. The optical system of claim 1, wherein the filter coating is located adjacent to one lens and/or in between two lenses of the lens system.

3. The optical system of claim 1, wherein the filter coating is located on an optical surface as support element of the optical system.

4. The optical system of claim 3, wherein the filter coating is located on a curved optical surface.

5. The optical system of claim 1, wherein the optical system comprises an optical plate as support element, and wherein the filter coating is arranged at least on one side of the optical plate.

6. The optical system of claim 1, wherein the angle of incidence of the image light on the first filter coating is less than 10° or more preferably near 0°.

7. The optical system of claim 1, wherein the filter coating is formed such that, in case of fluorescence imaging, an infrared or near infrared emission radiation is collectable by the image sensor free of an excitation radiation.

8. The optical system of claim 6, wherein the filter coating is formed such that, in case of fluorescence imaging, an infrared or near infrared emission radiation is collectable by the image sensor free of an excitation radiation.

9. The optical system of claim 1, wherein the filter coating is adapted to the angle of incidence of the image light to the one or more filter coatings and comprises a transmission characteristic varying from a center to a peripheral region of the one or more filter coatings.

10. The optical system of claim 1, wherein the micro-lens array has a chief ray angle function with a high maximum angle of incidence of greater than 30°.

11. The optical system of claim 10, wherein the filter coating, the lenses, and/or the support element are arranged such, that a path of rays of the optical system is adapted to the chief ray angle of the micro-lens array of the image sensor.

12. The optical system of claim 1, wherein the angle of incidence to the filter coating is smaller than a chief ray angle progression of the image sensor.

13. A video endoscope for collecting fluorescence imaging images comprising a handle; an elongate shaft; a distal end section, wherein the distal end section comprises an active pixel electronic image sensor with a progressive offset micro-lens array and a chief ray angle function with a maximum angle of incidence of at least 20°, and an optical system comprising a lens system with a first lens, a second lens, a third lens and/or further lenses in order from an object side to receive an image light from an object field and to direct the image light to the image sensor arranged in an image plane of the optical system; and at least one filter coating located at and/or on a support element for forming an interference filter at a position within the optical system, wherein an angle of incidence of the image light on the filter coating is minimized, thereby enabling reliable collection of fluorescence images.

14. The video endoscope of claim 13, wherein the video endoscope is operable for both visible light image acquisition and fluorescence light acquisition.

15. The video endoscope of claim 14, wherein the filter coating is located between two lenses of the lens system.

16. The video endoscope of claim 13, wherein the filter coating is deposited on a curved optical surface.

17. The video endoscope of claim 13, wherein the filter coating is an element of an optical plate.

18. The video endoscope of claim 13, wherein the angle of incidence to the filter coating is smaller than a chief ray angle progression of the image sensor.

19. The video endoscope of claim 13, wherein the filter coating, the lenses, and/or the support element are arranged such, that a path of rays of the optical system is adapted to the chief ray angle of the micro-lens array of the image sensor.

20. The optical system of claim 1, wherein the optical system comprises a second filter coating, a third filter coating, a fourth filter coating and/or further filter coatings.

* * * * *